US008206313B2

(12) United States Patent
Ballegaard

(10) Patent No.: US 8,206,313 B2
(45) Date of Patent: Jun. 26, 2012

(54) METHOD OF DETERMINING THE SYMPATHETIC TONE AND SYSTEM FOR MEASUREMENT THEREOF

(75) Inventor: Søren Ballegaard, Hellerup (DK)

(73) Assignee: ULL Meter A/S, Hellerup (DK)

( * ) Notice: Subject to any disclaimer, the term of this patent is extended or adjusted under 35 U.S.C. 154(b) by 1538 days.

(21) Appl. No.: 10/591,292

(22) PCT Filed: Mar. 3, 2005

(86) PCT No.: PCT/DK2005/000146
§ 371 (c)(1),
(2), (4) Date: Dec. 18, 2006

(87) PCT Pub. No.: WO2005/084529
PCT Pub. Date: Sep. 15, 2005

(65) Prior Publication Data
US 2007/0191916 A1    Aug. 16, 2007

(30) Foreign Application Priority Data

Mar. 3, 2004   (DK) ................................. 2004 00359
Apr. 5, 2004   (DK) ................................. 2004 00550

(51) Int. Cl.
*A61B 5/00* (2006.01)
*A61B 5/05* (2006.01)
*A61B 19/00* (2006.01)
(52) U.S. Cl. ......... 600/557; 600/552; 600/554; 128/898
(58) Field of Classification Search .......... 600/552–557; 128/898
See application file for complete search history.

(56) References Cited

U.S. PATENT DOCUMENTS

| 3,911,904 A | 10/1975 | Saba |
| 3,969,734 A | 7/1976 | Klein et al. |
| 4,570,640 A * | 2/1986 | Barsa ............................ 600/554 |

(Continued)

FOREIGN PATENT DOCUMENTS

CA     1013962     7/1977

(Continued)

OTHER PUBLICATIONS

Ekman et al., "Molecules in life and death," "Stress; Molecules, the Individual, Organisation and Society," Livers Publishing Firm, Stockholm 2002, pp. 77-79.

(Continued)

*Primary Examiner* — David Shay
(74) *Attorney, Agent, or Firm* — Birch, Stewart, Kolasch & Birch, LLP

(57) ABSTRACT

A method of determining the sympathetic tone, a system for applying and measuring a stimulation, and the use of a system for applying and measuring a stimulation for determining the sympathetic tone are provided. The method of determining the sympathetic tone includes the steps of: measuring an applied stimulation at a threshold value of the stimulation in one or more sympathetic tone-neutral points and measuring an applied stimulation at the same threshold value in one or more sympathetic tone-dependent points. The use of a system for applying and measuring a stimulation for determining the sympathetic tone includes the steps of: measuring an applied stimulation at a threshold value of the stimulation at one or more sympathetic tone-neutral points and measuring an applied stimulation at the same threshold value of the stimulation at one or more sympathetic tone-dependent points.

19 Claims, 5 Drawing Sheets

U.S. PATENT DOCUMENTS

| | | | |
|---|---|---|---|
| 5,038,795 A | | 8/1991 | Roush et al. |
| 5,381,805 A | * | 1/1995 | Tuckett et al. ............... 600/552 |
| 5,673,708 A | | 10/1997 | Athanasiou et al. |
| 5,922,018 A | | 7/1999 | Sarvazyan |
| 6,571,124 B1 | | 5/2003 | Storm |
| 2003/0105412 A1 | * | 6/2003 | Mauderli et al. .............. 600/555 |
| 2010/0016927 A1 | * | 1/2010 | Caparso et al. ................ 607/62 |

FOREIGN PATENT DOCUMENTS

| | | |
|---|---|---|
| EP | 0 236 513 A1 | 9/1987 |
| WO | WO-2005/084529 A2 | 9/2005 |

OTHER PUBLICATIONS

Hansen et al., "Evaluation of a radioimmunoassay and establishment of a reference interval for salivary cortisol in healthy subjects in Denmark," Scand J. Lab Invest 2003, 63: 303-10.

Normell et al., Measurement of skin temperature, :Sympathetic skin nerve activity and skin temperature changes in man, Acta Physiol Scand 1974; 91: 417-26.

Beijing College of Traditional Chinese Medicine: Essentials of Chinese Acupuncture, Beijing Foreign Languages Press, 1980.

Williams et al., Gray's Anatomy, New York: Churchill Livingstone, 1989; 723-1168.

F Mann, "Textbook of Acupuncture," William Heinemann Medical Books, London 1987; pp. 57-64.

Amit and Galina Physiol. Rev. 66: 1091-1120, 1986.

John D. Rutherford et. al., "Chronic Ischemic Heart Disease", vol. 2, Heart Disease: A Textbook of Cardiovascular Medicine, Third Edition, 1988, W. B. Saunders Company, pp. 1312-1378.

* cited by examiner

METHOD OF DETERMINING THE SYMPATHETIC TONE AND SYSTEM FOR MEASUREMENT THEREOF

TECHNICAL FIELD

The invention relates to a method of here-and-now determination of the sympathetic tone and a system for measurement thereof. As the method provides the person with a here-and-now determination of the sympathetic tone it is applicable for determining healthy individuals' level of potential for performing optimally both physically and mentally. The invention further relates to use of the system according to the invention for determining the sympathetic tone and use of measuring of the nociception for determining the sympathetic tone.

BACKGROUND ART

In mammals the nervous system is functionally divided into a somatic nervous system and an autonomic nervous system. The autonomic nervous system functions automatically and reflectory. The autonomic nervous system can further be divided into the counteracting sympathetic and parasympathetic systems. The sympathetic and parasympathetic nerves have opposite effects.

The sympathetic nervous system mobilizes the resources in the organism in a so-called "stress phase" such that an immediate dangerous situation/a challenge is handled in the optimum manner. This means that mentally the person thinks faster and more clearly at the same time as sharpening the ability to focus his/her thoughts. For supporting this purpose, irrelevant sense impressions are effectively impeded. Physically the body responds by lowering the response time, increasing the muscle strength, sharpening the senses, and optimizing the coordination between thought and motor skills.

In conclusion, the above entails that the "stress phase" is a positive physiological phenomenon, when it manifests itself in the right amount and in the right balance with the necessary recovery, which as described below is effected when the parasympathetic nervous system dominates.

The parasympathetic nervous system restores and builds up the organism's resources and thereby ensures that the necessary resources are available when they are to be mobilized in an acute stress situation.

Physiologically, simulation via the sympathetic nerves increases the pulse and the blood pressure and inhibits the secretion formation in the glands, etc., whereas the parasympathetic nerves inter alia lower the heart rate and the blood pressure and stimulate glands to secrete. During stress and in dangerous situations the sympathetic nervous system is activated.

Stress is a condition in which the resources of the organism are activated with a view to handling a situation which is perceived as dangerous or potentially dangerous by the brain. If the person has the necessary resources available, the situation is perceived in a positive manner. If the situation represents a state in which the strain exceeds the resources of the body, the organism's resources become taxed and longterm and intense stress will impair the person's performance. This state is called chronic or negative stress.

In its mildest form chronic stress manifests itself as moderate bodily symptoms such as muscle tension, fatigue or headache. In a more severe degree of stress additional symptoms are experienced in form of for instance memory problems, lack of concentration and distress from the internal organs (eg. palpitations, stomach ache, decreased libido). In an even more serious stress state, social ability is also impaired, eg reduced tolerance, irritability and uncontrolled bursts of anger. In the latter case, untreated chronic stress may lead to illness whereby the working capacity is lost for a period of time.

The body's reaction to the above strain is controlled by the hypothalamic-pituitary-adrenal system which activates the release of steroid hormones (glycocorticoids½) including cortisol. Additionally, other hormones are released among others catecholamines including dopamine, noradrenaline and adrenaline. As a result, a set of physiological reactions are created which in combination is called the response phase. Substantially all the systems of the body are affected including the brain, the cardiovascular system, the immune system, the respiratory system and the digestive system.

When the physical and mental dangers/challenges/strains have passed, the body's response thereto is inactivated and the recovery phase begins.

The stress reactions are not activated by purely physical or psychological threats, but also by our thoughts. A number of everyday-life situations inter alia rush for time, worries, personal relationship problems and financial worries, activates the response phase without the person being threatened. It is the accumulated effect of these minor but daily strains that lead to chronic stress.

As a part of avoiding that the stress condition develops and thus leads to negative implications, the determination of a person's acute or accumulated stress level is vital to allow for actions to be initiated which can reduce or completely remove the strains causing the stress or the person's readiness to handle these strains can be increased such that the negative stress-related consequences—both personal and social—may be averted and/or prevented. Stress cannot per se be considered an illness, but accumulated stress can make a person more susceptible to impacts which may develop into an illness.

A number of methods are known for determining the sympathetic tone (the activity of the sympathetic nervous system) as a measure of a person's stress level including measuring of cortisol in saliva, measuring of catecholamines (adrenaline and/or noradrenaline) and cortisol in serum as well as measuring of catecholamines in urine (Ekman R. and Lindstedt. G.: "Molekyler på liv og død" (molecules in life and death), in Ekman R. and Arnetz B. (red) "Stress; Molekyleme, Individen, Organisationen, Samhället" (stress; molecules, the individual, organisation and society), Libers publishing firm, Stockholm 2002, pages 77-89; Hansen A. M., Garde A. H., Christensen J. M., Eller N. H. & Nettestrøm B. "Evaluation of a radioimmunoassay and establishment of a reference interval for salivary cortisol in healthy subjects in Denmark", Scand J Lab Invest 2003; 63: 303-10.) "Måling af hudtemperatur" (measurement of skin temperature) (Normell L A, Wallin B G. "Sympathetic skin nerve activity and skin temperature changes in man". Acta Physiol Scand 1974; 91: 417-26) and sweat secretion are other known method for measuring stress.

The known methods of determining stress and sympathetic tone are encumbered by the drawbacks that either complicated technical analyses involving delays, communication and expenses are required or the methods are not unsusceptible to impacts/influences from the physical environment. Serum determination of for instance cortisol requires a laboratory analysis. Additionally one drawback of such a determination is that a change in the serum concentration of cortisol may rely on other causes than an increased level of stress. The sweat secretion determination is encumbered by the drawback that this determination may be highly unreliable, especially on a hot day where sweat secretion increases regardless of the person's level of stress.

A need thus exists for a fast, reliable and inexpensive method of determining the sympathetic tone as a measure of a person's potential to perform optimally both physically and mentally.

DESCRIPTION OF THE INVENTION

The present invention provides a method of determining the sympathetic tone. It is fast, simple, reliable and inexpensive and can be used as a measure of a person's acute and accumulated level of stress.

The invention further provides a system for carrying out the method.

In a first aspect, the invention relates to a method of determining the sympathetic tone including the steps of: measuring an applied stimulation at a threshold value of the stimulation in one or more sympathetic tone-neutral points and measuring an applied stimulation at the same threshold value of the stimulation in one or more sympathetic tone-dependent points.

In a second aspect, the invention relates to a method of quantitative determination of the sympathetic tone in a human being, said method including:
a) Storage of a calibration threshold value and a stimulation threshold value, where the calibration threshold value is a quantitative measure of a nociception threshold value in a sympathetic tone-dependent point on a human body and subsequently;
b) Calculation of an indication value of sympathetic tone by comparing the stimulation threshold value with the calibration threshold value, whereby the indication value of sympathetic tone is a measure of the sympathetic tone in the human being.

In a third aspect, the invention relates to a system for measuring the sympathetic tone in a human being, said system including:
a) Memory means for storing a nociception calibration threshold value determined in a sympathetic tone-neutral point on the human body and for storing a nociception stimulation threshold value determined in a sympathetic tone-dependent point on the human body;
b) An electronic circuit programmed to data process the nociception calibration threshold value and the nociception stimulation threshold value so as to obtain the measurement.

In a fourth aspect, the invention relates to a system for measuring the sympathetic tone in a human being, said system including a pressure base with a contact face adapted to exert an outer compressive force on the human body, a sensor for measuring the compressive force exerted by the pressure base on the body, an electronic circuit adapted to store a first measured compressive force and a second measured compressive force, respectively, and to calculate a read-out value as an expression of the ratio between the first measured compressive force and the second measured compressive force, and wherein the system includes a read-out unit for displaying the read-out value.

In a fifth aspect, the invention relates to use of a system according to the invention for applying and measuring a stimulation for determining the sympathetic tone including the steps of measuring an applied stimulation at a threshold value of the stimulation in one or more sympathetic tone-neutral points and measuring an applied stimulation at the same threshold value of the stimulation in one or more sympathetic tone-dependent points.

In a sixth aspect, the invention relates to use of measuring nociception for determining the sympathetic tone.

BRIEF DESCRIPTION OF THE DRAWINGS

The invention is explained in detail below with reference to the drawings, in which.

BEST MODE(S) FOR CARRYING OUT THE INVENTION

Definitions

Figure 1:
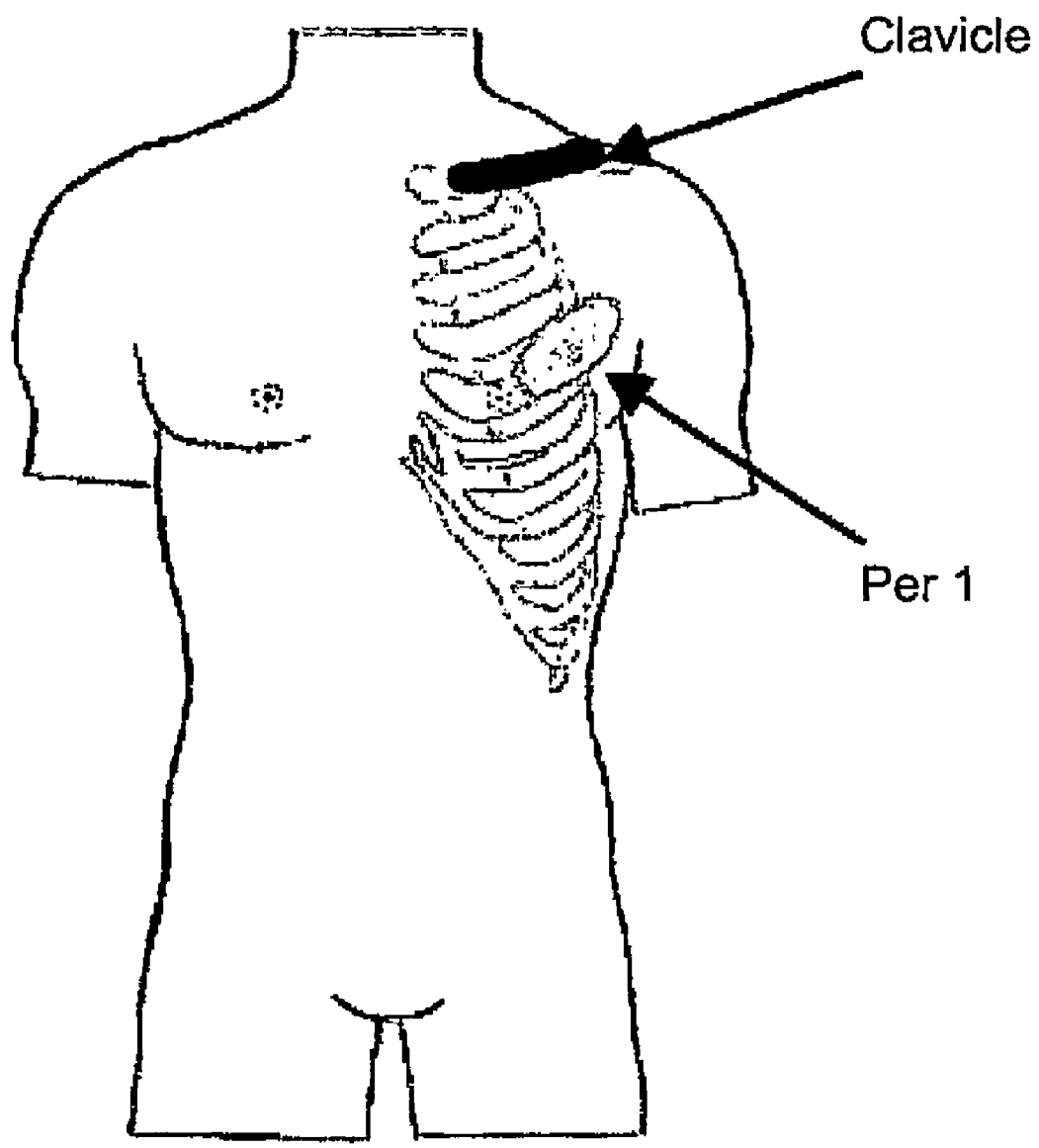
FIG. 1 shows the position of the sympathetic tone-neutral point anteriorly on the upper side of the clavicle, and the position of the sympathetic tone-dependent point, Per 1, the grey-shaded area, between the nipple and the anterior axillary fold, the black dot in the grey-shaded area indicating the most frequently used point within Per 1 according to the invention.

Prior to a detailed description of the invention, specific phrases relating to the aspects of the inventions are defined:

The phrase "stress" denotes a strain condition in which the strain exceeds the resources of the body. Stress has physical and emotional implications and may have positive and negative effects. An increased level of stress is expressed as an increased sympathetic tone.

The phrase "sympathetic tone" denotes the level of activity in the sympathetic part of the nervous system and is a measure of a person's potential to perform optimally both physically and mentally.

The phrase "acute stress" denotes a condition in which a person over a short period of time, typically hours/days, has experienced situations which have caused an increased activity in the sympathetic nervous system.

The phrase "accumulated stress" denotes a condition in which a person over a long period of time, typical weeks/months/years, has experienced situations which have caused an increased activity in the sympathetic nervous system.

The phrase "clinical stress" denotes a condition in which stress triggers clinical symptoms.

The phrase "physiological stress" denotes the determination of sympathetic tone.

The phrase "stimulation" denotes any type of stimulation which activates the skin's mechanoreceptors, thermoreceptor and/or nociceptive receptors. Stimulation may be provided as mechanical, thermal, radiation and/or chemical stimuli. A mechanical stimulation may for instance be provided by means of a compressive force. A thermal stimulation may for instance be provided by means of cold and/or heat. Radiation stimulation may for instance be provided by means of an applied infrared, visible and/or ultraviolet light or combined spectra thereof, eg. a laser, light-emitting diode, infrared, ultraviolet and/or white light source. Chemical stimulation may be provided by means of an organic and/or an inorganic compound.

The phrase "sympathetic tone-neutral point" denotes a point on the body in which the sensitivity to an applied stimulation is independent of the activity level of the sympathetic nervous system.

The phrase "sympathetic tone-dependent point" denotes a point on the body in which the sensitivity to an applied stimulation is dependent on the activity level of the sympathetic nervous system.

The phrase "threshold value of the simulation" denotes at which intensity the applied stimulation is to be applied to a given point in order for the person to perceive the applied stimulation as not pleasant, more specifically as unpleasant or as pain.

The phrase "threshold value of pressure sensitivity" denotes at which intensity the applied pressure is to be applied to a given point in order for a person to perceive the applied pressure as not pleasant, more specifically as unpleasant or as pain.

The phrase "nociception threshold value" denotes the threshold at which the person in the respective point perceives a stimulation as nociceptive, ie. as tissue-damaging. The expression also includes stimulation which is perceived as uncomfortable by the person.

The phrase "substantially at the same time" denotes that the measurings, eg. of the calibration threshold value and the stimulation threshold value, are performed within a period of a few minutes, eg. one minute, two minutes, three minutes, five minutes, ten minutes, fifteen minutes.

The phrase "significantly lower" means that the nociception threshold value in a sympathetic tone-dependent point is no more than 85%, particularly no more than 80%, and most particularly no more than 75%, of the threshold value in a sympathetic tone-neutral point.

The phrase "system for applying and measuring a stimulation" denotes a system, eg an apparatus or several apparatuses, which are able to apply and measure a stimulation.

The phrase "pressure-sensitive apparatus" denotes an apparatus which is able to apply and measure a pressure.

The phrase "marker" denotes a means marking a measuring point.

The phrase "measuring point" denotes a point whose threshold value of the stimulation at an applied stimulation is either neutral or dependent on the sympathetic tone.

Figure 3:
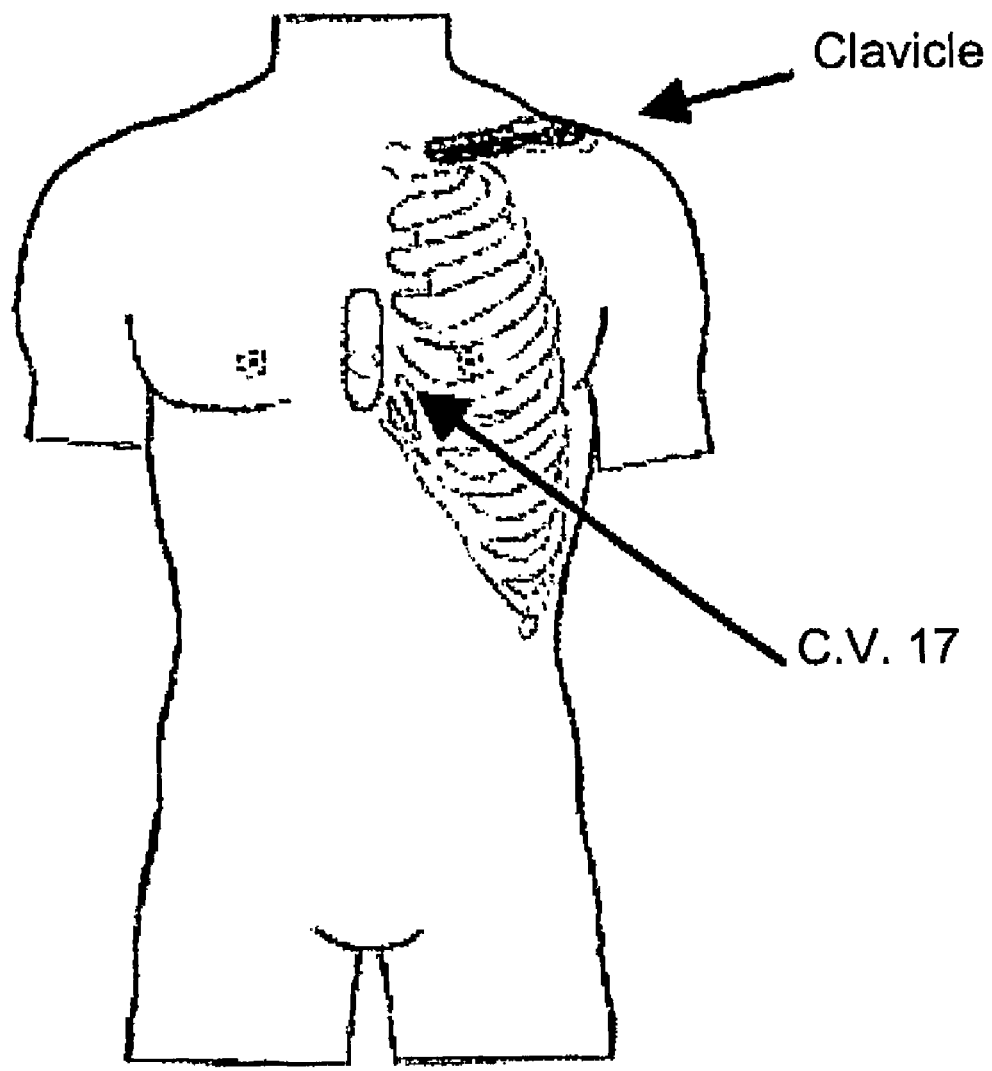
FIG. 3 shows the position of the sympathetic tone-neutral point anteriorly on the upper side of the clavicle, and the position of the sympathetic tone-dependent point, C.V. 17, the grey-shaded area, in the middle of the sternum, the black dot in the grey-shaded area indicating the most frequently used point within C.V. 17 according to the present invention.
Figure 4:
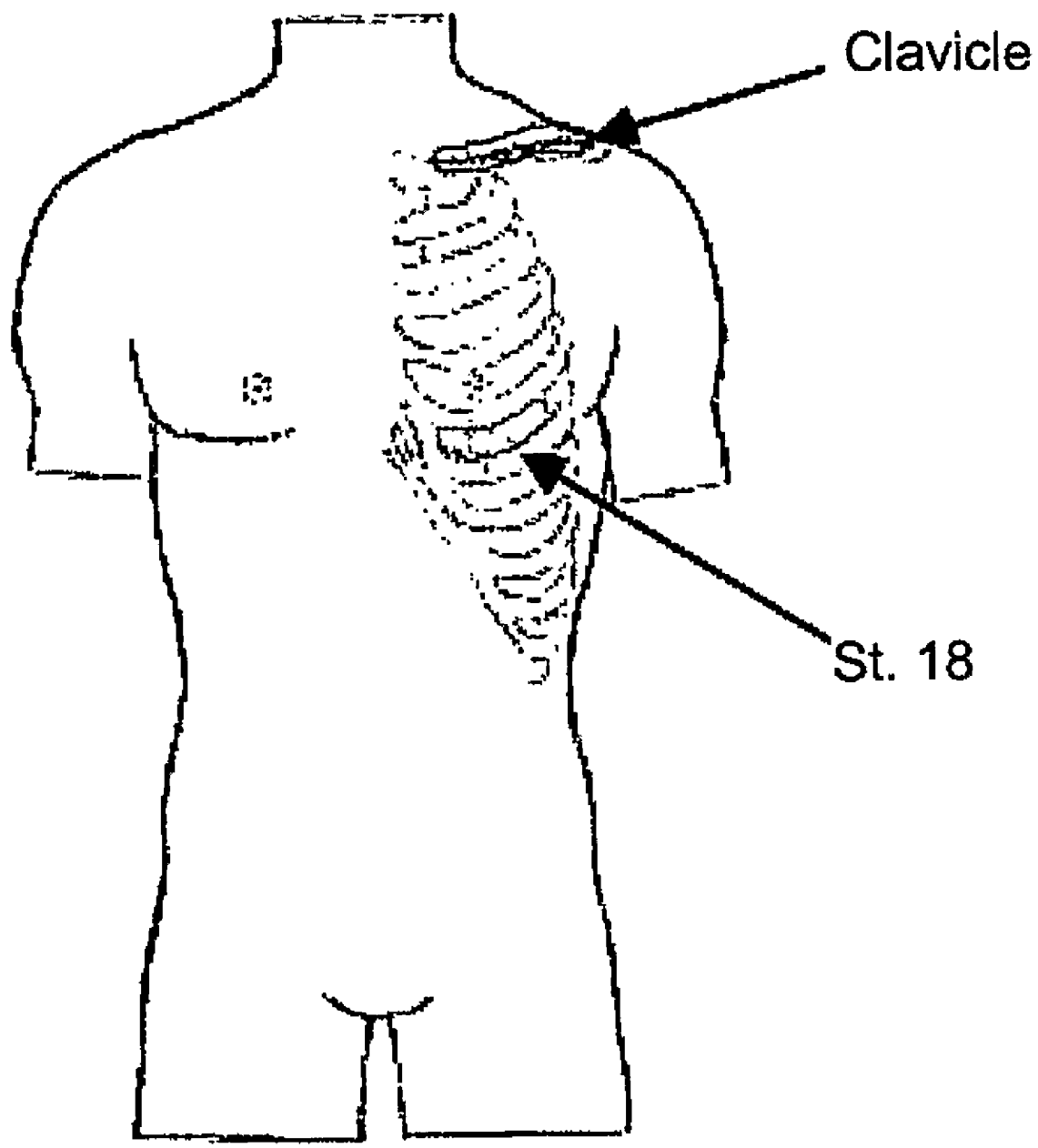
FIG. 4 shows the position of the sympathetic tone-neutral point, anteriorly, on the upper side of the clavicle, and the position of the sympathetic tone-dependent point, St 18, the grey-shaded area, between two ribs below the nipple, the black dot in the grey-shaded area indicating the most frequently used point within St 18 according to the invention.

The expressions "C.V. 17", "Per 1" and "St 18" denote meridian points pursuant to conventional Chinese theory (Beijing College of Traditional Chinese Medicine: Essentials of Chinese Acupuncture, Beijing Foreign Languages Press, 1980). C.V. is a conception vessel; Per is the pericardium and St is the stomach. The C.V. 17 point, the grey-shaded area, is shown in FIG. 3, where the most frequently used point according to the present invention within C.V. 17 in the grey-shaded area is indicated by the black dot. The Per 1 point, the grey-shaded area, is shown in FIG. 1, where the most frequently used point according to the present invention within Per 1 in the grey-shaded area is indicated by means of the black dot. The St 18 point, the grey-shaded area, is shown in FIG. 4, where the most frequently used point within St 18, in the grey-shaded area, is indicated by means of the black dot. The described points, C.V. 17, Per 1 and St 18, are well-defined according to their Chinese names and are in form of points on the surface of the body. In FIGS. 1, 3 and 4 grey-shaded areas are provided to mark that an actual area is to be examined and that the point merely is defined by its quality as being the most sore point when stimulated. This also means that the point may be outside the grey-shaded area marked on the drawings. In reality, the point may be at any position within the portion of the skin corresponding to the nerve supply to the heart of the sympathetic nervous system (as for instance stated in the following references: Rutherford J. D., Braunwald E. & Colin P. F., "Chronic heart disease"; Braunwald E., ed. "Heart Disease. A textbook of Cardiovascular Medicine". Philadelphia: W. B. Saunders Company, 1988; 1314-67; Williams P. L., Warwich R., Dyson M. & Bannister L. H., eds. Gray's Anatomy. New York: Churchill Livingstone, 1989; 723-1168; Mann, F., "Textbook of acupuncture", William Heinemann medical books, London 1987; 57-64).

Figure 2:
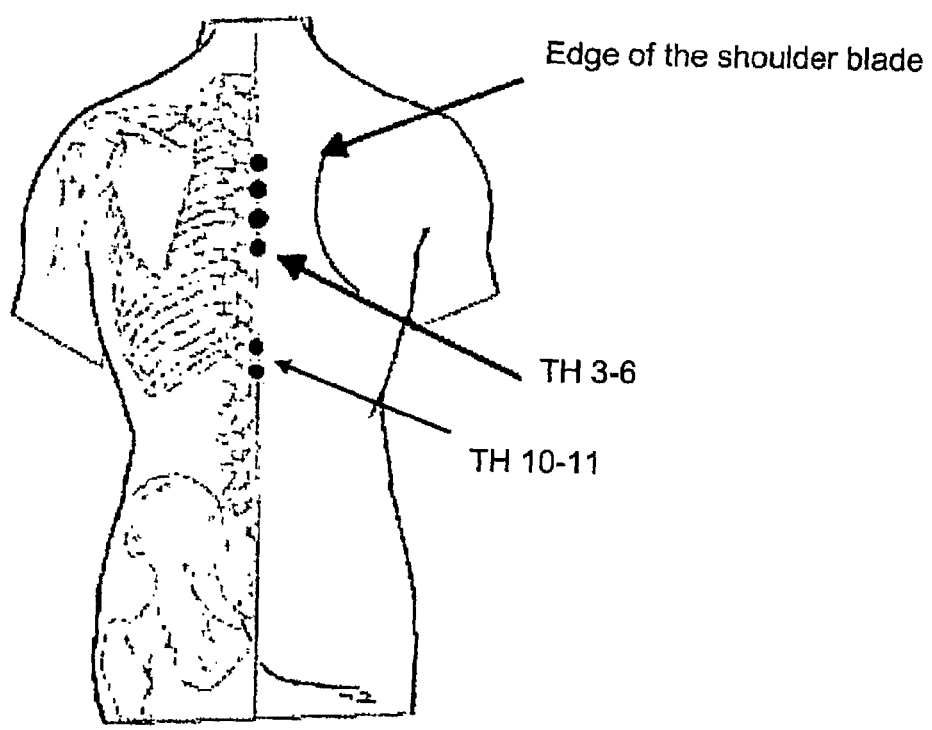
FIG. 2 shows the position of the sympathetic tone-neutral point posteriorly on the spinal column, more precisely at TH 10-11 and the position of the sympathetic tone-dependent point posteriorly corresponding to TH 3-6 in the area between the shoulder blades.

The expressions "TH 3-6" and "TH 10-11" denote the spinous processes 3-6 and the spinous processes 10-11, respectively, on the thoracic vertebrae of the same numbers. The spinous processes are the parts of the spinal column which feel like hard projections. The spinous processes 3-6 and the spinous processes 10-11 are shown in FIG. 2, the spinous processes 3-6 being the uppermost four black dots on the spinal column and the spinous processes 10-11 being the two lowermost dots on the spinal column.

For ensuring the optimum utilization of a person's total resources, in a given stress-evoking situation it is vital that this can be ensured by measuring the functional level of the nervous system at any given time.

The method according to the invention provides humans with such a tool in form of a method of determining the immediate (here-and-now) activity level of the sympathetic nervous system:

1) A low measured value denotes a low activity level in the sympathetic nervous system and is thus the best possible base for coping optimally with a future stressful situation.
2) A single high value provides the user with the information that the person—physiologically speaking—has mobilised the resources of the organism in a so-called "stress phase" with a view to coping with a situation which the brain perceives as dangerous or potentially dangerous.
3) Repetitive high measurements provide the user with the information that the person is in a prolonged "stress phase", which in the long run may tax the resources of the organism and provide a basis for a reduced functional level mentally, physically, emotionally and socially.
4) Varying high and low measurements provide the user with the information that the person is in situations in which the "stress phase" alternately is activated and inactivated. As a result a possibility for learning and awareness exists.

In a specific embodiment, the method is thus linked to special tools and educational programmes which based on the actual measurement can teach the person how to prevent and treat negative stress and teach the person what specifically increases/reduces the stress level in him/her.

The present invention is the result of intensive research in methods for determining the activity level of the sympathetic nervous system and thus a person's potential to perform optimally both physically and mentally and neatly solves the problems of the known methods of determining the sympathetic tone, which is precisely a measure of the activity level of the sympathetic nervous system, here referred to as physiological stress.

According to the present invention, it has surprisingly been found that points on the body exist, whose threshold value of a stimulation when this is applied to the point is sympathetic tone-neutral, while other points are sympathetic tone-dependent. In other words, certain points exist, where the sensitivity to an applied stimulation is independent of the activity level of the sympathetic nervous system, while there are other points, where the sensitivity to an applied stimulation is dependent on the activity level of the sympathetic nervous system. According to the invention, a person's sensitivity to the applied stimulation in a sympathetic tone-dependent point increases when the activity level of the sympathetic nervous system also increases. This realization is surprising in that it has previously been described that stress and thus increased sympathetic tone generally increases the tolerance to pain (Amit and Galina, Physiol. Rev. 66: 1091-1120, 1986). The identified sympathetic tone-dependent points thus respond differently than what is known for the body in general.

By measuring which intensity of an applied stimulation is necessary to obtain a threshold value of the stimulation in a sympathetic tone-neutral point and comparing this with the necessary intensity of an applied stimulation to obtain the same threshold value of the stimulation in a sympathetic tone-dependent point, a physiological measure of the sympathetic tone and thus of the person's physiological stress or immediate stress level is obtained. The measurement may be considered as a here-and-now determination of the activity level of the sympathetic nervous system.

When using the method according to the invention to determine the immediate or acute stress level, the method provides the person with a tool for adjusting the stress state and thereby optimizing his/her performance. An acute increase in the activity level of the sympathetic nervous system may have a beneficial effect on the person's performance. It is thus well known that an increased adrenaline level may be beneficial for optimising the performance. The method according to the invention is thus used to adjust the sympathetic tone such that an increased activity level of the sympathetic nervous system is obtained resulting in a beneficial effect.

A method of determining the immediate activity level of the sympathetic nervous system is thus provided, said activity level being significant to the person's ability or potential to perform optimally. The method may be of a diagnostic nature and have diagnostic value, but it may also be described as a prognostic method in that it provides the person with a prognosis of the person's immediate potential to perform optimally. As mentioned in the introduction, the sympathetic nervous system mobilises the resources of the organism in a so-called "stress phase" such that an actual dangerous situation/challenge is handled in the best possible manner. This means that mentally the person thinks faster and more clearly at the same time as the ability to focus his/her thoughts is increased. For supporting this purpose, irrelevant sense impressions are effectively impeded. Physically the body responds by lowering the response time, increasing the muscle strength, sharpening the senses, and optimizing the coordination between thought and motor skills.

A test among healthy randomly selected persons reveals that half of the persons which are heavily stressed, ie. in a stress group level 3 as defined below, perceive themselves as being unstressed. As a result, the present method and measuring tool are of great practical value by providing the person with vital information to which the person otherwise would not have access.

The method according to the invention may also be used to record the activity level of the sympathetic nervous system on a long-term basis and may thus be effective for preventing in time that such a state lead to stress-related complications. Such recordings may for instance be forwarded to a central register/data centre monitoring the data of the individual person and in time sends a warning back to the person, whereby the said complications can be avoided.

According to the invention the stimulation sensitivity in the points may vary highly from one person to the next and a single determination of the sympathetic tone for a given person cannot necessarily be related to the actual stress state of the person unless the person's normal state is known. It may thus be necessary to supplement the determination of the sympathetic tone with additional information. A low activity level of the sympathetic nervous system (ie. small difference between the two determinations) thus indicates an optimum prognostic utilization of the person's resources. A high activity level (ie. large difference between the two determinations) is, however, not unambiguous, but requires additional information. A situation, where a high activity level is determined by means of the method, may thus occur, while an additional analysis by means of a stress form (questionnaire) reveals that the person displays no sign of clinical stress. In this case the measurement reflects acute stress and not chronic stress.

According to the invention a stimulation may be any type of stimulation activating the skin's mechanoreceptors, thermoreceptor and/or nociceptive receptors. Stimuli may be provided as mechanical, thermal, radiation and/or chemical stimulus. A mechanical stimulation may for instance be provided by means of a compressive force. A thermal stimulation may for instance be provided by means of cold and/or heat. Radiation stimulation may for instance be provided by means of an applied infrared, visible and/or ultraviolet light or combined spectra thereof, eg. a laser, light-emitting diode, infrared, ultraviolet and/or white light source. Chemical stimulation may be provided by means of an organic and/or an inorganic compound.

The recorded physiological measure of the sympathetic tone is a total measure of the sum of the person's acute stress level and the person's accumulated stress level. The method according to the invention also allows for the recordal of the effect of any intervention/stress-reducing initiatives.

The threshold value of the stimulation is obtained when the person, to whom a stimulation is applied to a specific point no longer perceives the applied stimulation as comfortable, more specifically when the person perceives the applied stimulation as unpleasant or as pain.

Sympathetic tone-neutral points may also be denoted as calibration points. These points may be located anteriorly on the upper side of the clavicle and posteriorly on the spinal column, specifically denoted as TH 10-11.

Sympathetic tone-dependent points may also be denoted as recording points. These points may be located anywhere on the skin which innervationally correspond to the nerve supply of the sympathetic nervous system to the heart, eg. anteriorly, to which three points are connected: C.V. 17 in the middle of the sternum, ST 18 between two ribs below the nipple and Per 1 between the nipple and the anterior axillary fold and posteriorly corresponding to TH 3-6 in the area between the shoulder blades. According to an embodiment the most sore point of the said points is preferably chosen, such a point rendering the most accurate representation of the activity level.

The present invention allows for an overall measure of a person's acute stress over a short period of time, eg. hours/days, as well as of the accumulated stress over a long period of time, eg months/years.

The distinction between acute and accumulated stress may be carried out by means techniques known to the person skilled in the art. These techniques include without being limited thereto: conversations about the person's physical and mental state or other manners in which the state can be elucidated optionally by filling in a stress form (questionnaire). Furthermore, the causes of stress can be found by means of techniques which are known to the person skilled in the art. These techniques include without being limited thereto: a conversation about the person's physical and mental state or other maimers in which the state can be elucidated optionally by filling out a stress/resource balance sheet. This is briefly discussed above as supplement of additional information to the determination according to the invention.

The first clinical signs of chronic stress are fatigue and increased muscle tension in the muscles of the motor apparatus. It can manifest itself as for instance headache and back, shoulder and neck pains. This state is harmless and is experienced in many of the situations which are perceived as positive stress.

In case of prolonged stress loads, additional symptoms are triggered in the portions of the nervous system which are not under the power of the will, viz. the autonomic nervous system. These symptoms may for instance manifest themselves as moodiness, stomach ache, palpitations and lack of concentration.

If the stress load is further exacerbated, additional symptoms to the above symptoms are triggered in the portions of the nervous system which are under the power of the will. A person is for instance no longer able to control his/her anger or irritability and the social behaviour is negatively affected.

The measuring of which intensity of an applied stimulation is necessary to obtain a threshold value of the stimulation can be determined by using a system capable of measuring the intensity of the applied stimulation. One example of such a system for measuring an applied stimulation is a system capable of measuring an applied mechanical stimulus, an applied thermal stimulus, an applied radiation stimulus and/or a chemical stimulus. A system for measuring an applied mechanical stimulus may for instance be an apparatus for measuring an applied compressive force, said apparatus for instance being a manometer. After tests with for instance an apparatus capable of measuring an applied compressive force, the measuring of which intensity of an applied compressive force is necessary to obtain a threshold value of the pressure sensitivity can be performed with a finger.

The method according to the invention may furthermore be used as a measure of the effect of various initiatives. These initiatives, which are unrelated to professional health treatment, may for instance include initiatives corresponding to the situations perceived as stress-evoking.

The method according to the invention may be carried out by a person other than the person being measured or by the person being measured. The most accurate measurement is obtained when the person himself/herself performs the determination.

Comprehensive studies have now revealed that the levels of activity of the sympathetic nervous system (Level 0-3) can be correlated in the following manner to which stimulation in form of an applied compressive force is necessary to obtain a threshold value of the pressure sensitivity in a sympathetic tone-neutral in relation to which stimulation in form of an applied compressive force is necessary to obtain the same threshold value of the pressure sensitivity in a sympathetic tone-dependent point:

Level 0: When the applied compressive force at a threshold value of the pressure sensitivity in a sympathetic tone-dependent point exceeds or is equal to 80% of the applied compressive force at the same threshold value of the pressure sensitivity in a sympathetic tone-neutral point.

Level 1: When the applied compressive force at a threshold value of the pressure sensitivity in a sympathetic tone-dependent point is between 55% and less than 80% of the applied compressive force at the same threshold value of the pressure sensitivity in a sympathetic tone-neutral point.

Level 2: When the applied compressive force at a threshold value of the pressure sensitivity in a sympathetic tone-dependent point is between 30% and less than 55% of the applied compressive force at the same threshold value of the pressure sensitivity in a sympathetic tone-neutral point.

Level 3: When the applied compressive force at a threshold value of the pressure sensitivity in a sympathetic tone-dependent point is less than 30% or the applied compressive force at the same threshold value of the pressure sensitivity in a sympathetic tone-neutral point.

The above ratios between the level of activity of the sympathetic nervous system and the applied compressive force at a threshold value of the pressure sensitivity in a sympathetic tone-dependent point in relation to the applied compressive force at the same threshold value of the pressure sensitivity in a sympathetic tone-neutral point may vary from one person to the next. In a few cases the variation may be up to about 90%.

In the same person, the measurements may furthermore vary between the different sympathetic tone-dependent points and between the different sympathetic tone-neutral points. In order to obtain the most accurate determination of the activity level of the sympathetic nervous system it is thus vital to choose a sympathetic tone-neutral point, which is not sensitive due to other factors.

The above correlation between which applied compressive force is necessary to obtain a threshold value of the pressure sensitivity in a sympathetic tone-neutral point in relation to which applied compressive force is necessary to obtain the same threshold value of the pressure sensitivity in a sympathetic tone-dependent point has also been found to apply when a thermal, radiation or chemical stimulus is used. As an example it has been found that when an applied compressive force is used, a sympathetic tone-dependent point is more sensitive to for instance heat and cold, the heat for instance being transferred by heat conduction or by radiation, said point also being more sensitive to influences from organic and/or inorganic compounds than a sympathetic tone-neutral point.

Any sympathetic tone-neutral point can be used with any sympathetic tone-dependent point. The use of sets of a sympathetic tone-neutral point and a sympathetic tone-dependent point either anteriorly or posteriorly is preferred. As an example, it is preferable to use the sympathetic tone-neutral point anteriorly on the upper side of the clavicle in combination with the sympathetic tone-dependent points C.V. 17 or St 18 or Per 1 or preferable to use the sympathetic tone-neutral point TH 10-11 in combination with the sympathetic tone-dependent point TH 3-6.

The invention relates to a method of determining the sympathetic tone including the steps of: measuring an applied stimulation at a threshold value of the stimulation in one or more sympathetic tone-neutral points and measuring an applied stimulation at the same threshold value in one or more sympathetic tone-dependent points.

According to a particular embodiment of the invention, an applied stimulation may be provided by an applied mechanical, thermal, radiation and/or chemical stimulus.

According to a particular embodiment of the invention a mechanical stimulus may be provided by an applied compressive force.

According to a particular embodiment of the invention, a thermal stimulus may be provided by an applied heat or cold source.

According to a particular embodiment a radiation stimulus may be provided by means of an applied infrared, visible and/or ultraviolet light or combined spectra thereof, eg. a laser, light-emitting diode, infrared, ultraviolet and/or white light source.

According to a particular embodiment of the invention a chemical stimulus may be provided by an applied organic and/or inorganic compound.

According to a particular embodiment of the invention, the determination of an applied stimulation at a threshold value of the stimulation may be carried out by means of a system for measuring the applied stimulation.

According to a particular embodiment of the invention, the measuring of the applied stimulation at a threshold value of the stimulation in a sympathetic tone-neutral point may be performed anteriorly on the upper side of the clavicle and/or posteriorly on the spinal column corresponding to TH 10-11.

According to a particular embodiment of the invention, the measuring of the applied stimulation at a threshold value of the stimulation in a sympathetic tone-dependent point may be carried out at one or more locations on the skin which innervationally correspond to the nerve supply of the sympathetic nervous system to the heart, eg. in one or more of the anterior points to which three locations are connected: C.V. 17 in the middle of the sternum, ST 18 between two ribs below the nipple and Per 1 between the nipple and the anterior axillary fold and posteriorly corresponding to TH 3-6 in the area between the shoulder blades, where the most sore of the said points is chosen.

According to a particular embodiment of the invention it relates to a method for quantitative determination of the sympathetic tone in a human, said method including:
a) storage of a calibration threshold value and a stimulation threshold value, the calibration threshold value being a quantitative measure of a nociception threshold value in a sympathetic tone-neutral point on a human body and the stimulation threshold value being a quantitative measure of a nociception threshold value in a sympathetic tone-dependent point on the human body and subsequently:
b) calculation of an indication value of the sympathetic tone by comparing the stimulation threshold value with the calibration threshold value, whereby the indication value of sympathetic tone is a measure of sympathetic tone in the human being. In an embodiment, the calibration threshold value and the stimulation threshold value are measured substantially simultaneously. The calibration threshold value may, however, also represent a historic mean value obtained on the basis of previous measurements or a predetermined value such as a constant which for instance may represent an average value of a number of different persons.

In an embodiment nociception is induced by means of a exposure to compressive force, heat, cold, radiation, chemical stimulus or combinations thereof.

According to an embodiment, a significantly lower nociception threshold value in a sympathetic tone-dependent point than in a sympathetic tone-neutral point indicates that a person has increased sympathetic tone.

The determined indication values of the sympathetic tone can be recorded either here-and-now or over a lengthy period of time. A particular embodiment thus relates to a method in which the indication value of the sympathetic tone is compared to at least one previously determined indication value of the sympathetic tone, said previous value indicating sympathetic tone at a earlier point in time.

The invention also relates to a system for measuring the sympathetic tone in a human being, said system including:
a) Memory means for storing a nociception calibration threshold value determined at a sympathetic tone-neutral point on the human body and for storing a nociception stimulation threshold value in a sympathetic tone-dependent point on the human body;
b) An electronic circuit programmed to data process the nociception calibration threshold value and the nociception stimulation threshold value so as to obtain the measurement.

In an embodiment, the system according to the invention may further include user-operated means for applying a discomfort-inducing stimulus to the surface of the human body and user-operated storage means adapted to:
a) store the nociception calibration threshold value resulting from a first user operation;
b) store the nociception stimulation threshold value resulting from a second user operation.

The means for applying a discomfort-evoking stimulus may be contained in a first unit and said electronic circuit may be contained in another unit. For obtaining the necessary data transfer between the first and second units the units may for instance be provided with means for wireless communication. In a so-called "distributed system" the first unit may for instance be a hand-held unit, which the user easily can bring with him/her, while the other unit may be a central computer at a doctor or hospital, said computer collecting data from a number of different users which each has a hand-held unit. Optionally the computer may be placed in the home of the user. In a distributed system a mobile phone may advantageously be used as communications means for transferring data from the hand-held unit to the computer, the hand-held unit for instance wirelessly transmitting data to the computer via a conventional mobile phone signal. This signal may be forwarded by a mobile phone provider to the computer via the internet. Optionally the second unit may be formed of a programmed mobile phone for instance communicating with the first unit via Bluetooth™, in which case a system utilizing the computing strength and memory storage of the mobile phone is used instead of a distributed system.

In a second embodiment, the means for applying a discomfort-evoking stimulus and the said electronic circuit are integrated in one and the same apparatus.

In an embodiment, the means for applying a discomfort-provoking stimulus are adapted to apply a stimulus which is gradually increased, the storage means being adapted to store a stimulation level at a moment in time corresponding to the first and second user operation, respectively.

In an embodiment the invention relates to a system in which the applied discomfort-evoking stimulus includes exposure to compressive force, heat, cold, radiation, chemical stimulus or combinations thereof.

In an embodiment the pressure may be applied by means of a pressure base or a clamp.

In a particular embodiment of the system, the applied discomfort-inducing stimulus is stopped at the time of the first or the second user operation.

The contact face of the pressure base is resilient in a particular embodiment.

In further embodiment the pressure base contains a liquid, a gel and optionally gas-filled bubbles.

In a particular embodiment the contact face on the pressure base is less than 4 cm$^2$, preferably between 1 and 2 cm$^2$.

The invention further relates to a system for applying and measuring a stimulation to determine the sympathetic tone, said system including a measuring unit and a read-out unit displaying the applied stimulation.

According to a particular embodiment of the invention, the system includes a marker for marking the measuring points such that it can be established where the stimulation was applied.

According to a particular embodiment of the invention, the system is provided with a scale divided into at least two zones, particularly four zones, which each for instance relates to the above levels of stress 0, 1, 2 and 3.

According to a particular embodiment of the invention these zones may have different colours, patterns or other distinctive marks which make them distinguishable from each other.

The system according to the invention includes a pressure base with a contact face adapted to exert an outer compressive force on the human body, a sensor for measuring the compressive force exerted by the pressure base on the body, an electronic circuit adapted to store a first measured compressive force and a second measured compressive force, respectively, and to calculate a read-out value as an expression of the ratio between the first measured compressive force and the second measured compressive force, the system also including a read-out unit for displaying the read-out value. If the first measured compressive force is the measuring performed in a sympathetic tone-neutral point and the second measured compressive force is the measuring performed in a sympathetic tone-dependent point, the level of activity of the sympathetic nervous system is displayed as the read-out value.

The contact face of the pressure base may be resilient. As a result a more accurate measurement is obtained, the contact face being adaptable to uneven areas on the body and provides a uniform pressure. The pressure thus corresponds to the applied force divided by the area of the contact face.

The pressure base may contain a liquid, a gel and optionally gas-filled bubbles, whereby a particularly snug fit to the surface of the body is obtained in the measuring point.

According to an embodiment the area of contact face on the pressure base may be less than 4 cm$^2$, preferably between 1 and 2 cm$^2$.

The sensor may be a piezoresistive force sensor.

The system may be integrated in an apparatus preferably being hand-held and power-supplied by one or more batteries. As a result the user may bring the apparatus along on travels.

The read-out unit is an electronic display.

The electronic circuit may be adapted to determine the read-out value as one of a number, eg. four, discrete read-out values (0, 1, 2, 3), the ratio between the first measured value and the second measured value being rounded off to or allocated a discrete read-out value (0, 1, 2, 3) displayed on the read-out unit.

The discrete read-out value (0, 1, 2, 3) may be non-proportional to the ratio between the first measured value and the second measured value. The apparatus may thus be accommodated to a lacking proportionality or linearity between the measuring results and the level of activity of the sympathetic nervous system. The level 0 may thus correspond to the second measured compressive force being 80% or more of the first measured compressive force, level 1 may correspond to the second compressive force being 55-80% of the first compressive force, level 2 may correspond to the second measure compressive force being 30-55% of the first compressive force, and level 3 may correspond to the second measure compressive force being 30% or less than the first compressive force.

The electronic circuit may be adapted to calculate the first measured value as an average of a number of measured values and calculate the second measured value as an average of a number of measured values. A more reliable measurement of the person's stress level is thus obtained, the error indication of the read-out value caused by measurement uncertainty at the individual measurings being reduced.

Figure 5:
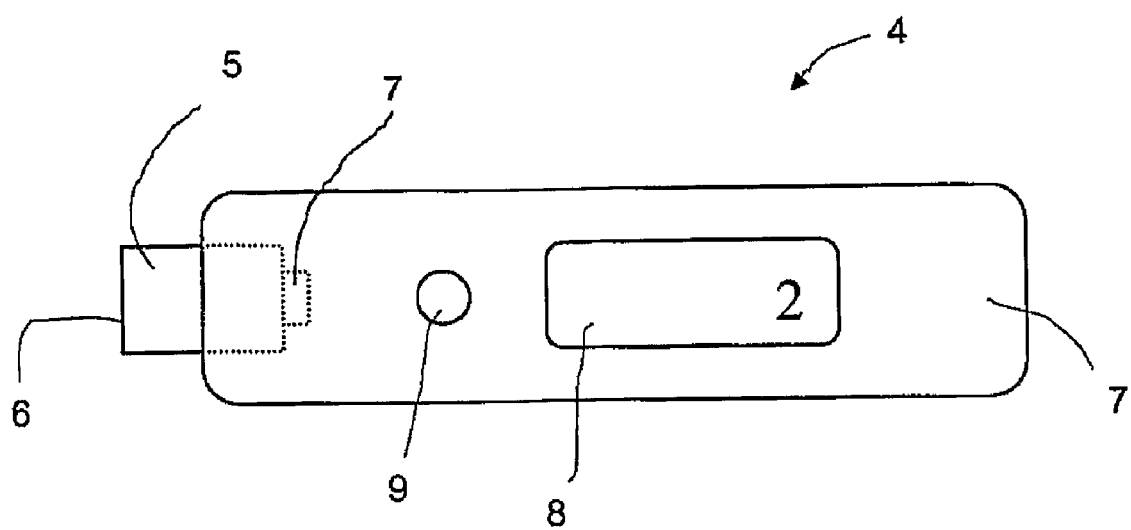
FIG. 5 shows a system according to the invention, the parts of the system being shown as integrated in one and the same apparatus. The apparatus includes a pressure base with a contact face adapted to exert an outer compressive force on a human's body, a sensor for measuring the compressive force exerted on the body by the pressure base. The apparatus includes a read-out unit for displaying the read-out value.

FIG. 5 shows a system according to the invention, the system being shown as integrated in one and the same apparatus for reason of clarity. The apparatus is hand-held and includes a housing 7, an electronic display 8, a control button 9 and a pressure base 5 extending from one end of the housing 7. The free end of the pressure base 5 has a contact face 6. Inside the apparatus the pressure base 5 abuts a force sensor or pressure sensor 7 connected to a not-shown electronic circuit. The electronic circuit is capable of storing the force or pressure measurements detected by the sensor 7. The circuit 7 is further capable of making calculations and transmitting a read-out value to the electronic display 8. A not-shown battery supplies the circuit with power.

In use, the person holds the apparatus in his/her hand and exerts an increasing pressure on a sympathetic tone-neutral point on the body until the threshold value of discomfort has been reached. The electronic circuit records the maximum compressive force detected by the sensor. The person pushes the control button 9 and then exerts an increasing pressure on a sympathetic tone-dependent point on the body until the threshold value of discomfort is reached. The electronic circuit records the maximum compressive force. When the control button 9 has been pushed, the circuit calculates a read-out value as an expression of the ratio between the first measured compressive force and the second measured compressive force. In this example, the read-out value is 0, 1, 2 or 3, if the second measured compressive force is more than 80%, 55-80%, 30-55%, respectively, or less than 30% of the first compressive force. The apparatus may optionally be adapted to determine a mean value of a number of measurements of the first compressive force and a mean value of a number of measurements of the second compressive force, the read-out value being determined on the basis of these mean values. FIG. 5 shows a measuring in which the activity level of the sympathetic nervous system is 2 corresponding to the compressive force on the sympathetic tone-dependent point at discomfort being between 30% and 55% of the compressive force on the sympathetic tone-neutral point.

According to a particular embodiment of the invention, said system may apply and measure a thermal stimulus, eg heat or cold.

According to a particular embodiment of the invention, said system may apply and measure a radiation, eg. an infrared, visible and/or ultraviolet light or combined spectra thereof, provided as an example by means of a laser, light-emitting diode, infrared, ultraviolet and/or white light source.

According to a particular embodiment of the invention, said system may apply and measure a chemical stimulus, eg. an organic or inorganic compound.

The invention further relates to the use of a system for applying and measuring a stimulation for determining the sympathetic tone including the steps of: measuring an applied stimulation at a threshold value of the stimulation in one or more sympathetic tone-neutral points and measuring an applied stimulation at the same threshold value of the stimulation in one or more sympathetic tone-dependent points.

According to a particular embodiment of the invention, a system is used for applying and measuring a stimulation for determining sympathetic tone, the measuring of an applied stimulation at a threshold value of the stimulation in one or more sympathetic tone-neutral points being performed anteriorly on the upper side of the clavicle and/or posteriorly on the spinal column corresponding to TH 10-11.

In an embodiment, the invention relates to use of a system for applying and measuring a stimulation for determining sympathetic tone, the measurement of an applied stimulation at a threshold value of the stimulation in one or more sympathetic tone-dependent points being performed at one or more locations on the skin which innervationally (ie relating to the nerve supply) correspond to the nerve supply of the sympathetic nervous system to the heart, eg. in one or more of the points contained in the areas: C.V. 17 in the middle of the sternum, ST 18 between two ribs below the nipple and Per 1 between the nipple and the anterior axillary fold and on the back corresponding to TH 3-6 in the area between the shoulder blades, where the most sore of the said points is chosen.

According to a particular embodiment of the invention a system is used which is capable of applying and measuring a mechanical stimulus such as a compressive force. According to a particular embodiment of the invention a system is used which is capable of applying and measuring a thermal stimulus such as heat or cold.

According to a particular embodiment of the invention, a system is used which is capable of applying and measuring radiation, eg. infrared, visible and/or ultraviolet light or combined spectra thereof, provided as an example in form of a laser, light-emitting diode, infrared, ultraviolet and/or white light source.

According to a particular embodiment of the invention a system is used which is capable of applying and measuring a chemical stimulus such as an organic or inorganic compound.

The invention is further illustrated in the following examples:

EXAMPLES

Unit in all measurements in the examples when measuring an applied compressive force by means of a manometer is British pounds (lbs)/cm², in the following referred to as lbs.

Units in all measurements in the examples when measuring a compressive force applied with a finger at the threshold value of the pressure sensitivity are: 0, +, ++, +++, where 0 is the applied compressive force at a threshold value of the pressure sensitivity in a sympathetic tone-neutral point, and where =, +, ++, +++ is the compressive force applied with a finger at the same threshold value of the pressure sensitivity in a sympathetic tone-dependent point, where 0 equals the applied compressive force in a sympathetic tone-neutral point, and +, ++, +++ is the relatively lower applied compressive force.

Example 1

Example 1a

The sympathetic tone of a person was determined in the following manner: By means of a manometer at a threshold value of the pressure sensitivity in the sympathetic tone-neutral point anteriorly on the upper side of the clavicle, the applied compressive force was measured to 13.8 lbs. Then the applied compressive force was measured to 13.0 lbs at the same threshold value of the pressure sensitivity in the sympathetic tone-dependent point C.V. 17. At the same threshold value of the pressure sensitivity in the sympathetic tone-dependent point the applied compressive force was thus 94% of the applied compressive force in the sympathetic tone-neutral point. According to the present invention this corresponds to Level 0 stress. The person then filled-in a questionnaire about the person's stress level, said questionnaire confirming that the person displayed no signs of clinical stress.

Example 1b

The sympathetic tone of another person was determined in the following manner. By means of a manometer at a threshold value of the pressure sensitivity in the sympathetic tone-neutral point anteriorly on the upper side of the clavicle, the applied compressive force was measured to 14.3 lbs. Then the applied compressive force was measured to 11.0 lbs at the same threshold value of the pressure sensitivity in the sympathetic tone-dependent point C.V. 17. At the same threshold value of the pressure sensitivity in the sympathetic tone-dependent point the applied compressive force was thus 77% of the applied compressive force in the sympathetic tone-neutral point. According to the present invention this corresponds to Level 1 stress.

Example 1c

The sympathetic tone of a third person was determined in the following manner. By means of a manometer at a threshold value of the pressure sensitivity in the sympathetic tone-neutral point anteriorly on the upper side of the clavicle, the applied compressive force was measured to 10.0 lbs. Then the applied compressive force was measured to 7.0 lbs at the same threshold value of the pressure sensitivity in the sympathetic tone-dependent point Per 1. At the same threshold value of the pressure sensitivity in the sympathetic tone-dependent point the applied compressive force was thus 70% of the applied compressive force in the sympathetic tone-neutral point. According to the present invention this corresponds to Level 1 stress.

Example 1d

The sympathetic tone of a fourth person was determined in the following manner: By means of a manometer at a threshold value of the pressure sensitivity in the sympathetic tone-neutral point posteriorly on the spinal column corresponding to TH-10-11 the applied compressive force was measured to 24.0 lbs. The the applied compressive force at the same threshold value of the pressure sensitivity in the sympathetic tone-dependent point posteriorly on the spinal column corresponding to TH 3-6 was measured to 22.5 lbs. At the same threshold of the pressure sensitivity in the sympathetic tone-dependent point, the applied compressive force was thus 94% of the applied compressive force in the sympathetic tone-neutral point. According to the present invention this corresponds to Level 0 stress. The person then filled-in a questionnaire about the person's stress level, said questionnaire confirming that the person displayed no signs of clinical stress.

Example 2

Example 2a

The sympathetic tone of a person was determined in the following manner: By means of a manometer at a threshold value of the pressure sensitivity in the sympathetic tone-neutral point anteriorly on the upper side of the clavicle, the applied compressive force was measured to 17 lbs. Then the applied compressive force was measured to 8.0 lbs at the same threshold value of the pressure sensitivity in the sympathetic tone-dependent point C.V. 17. At the same threshold value of the pressure sensitivity in the sympathetic tone-dependent point the applied compressive force was thus 47% of the applied compressive force in the sympathetic tone-neutral point. According to the present invention this corresponds to Level 2 stress.

Example 2b

The sympathetic tone of another person was determined in the following manner. By means of a manometer at a threshold value of the pressure sensitivity in the sympathetic tone-neutral point anteriorly on the upper side of the clavicle, the applied compressive force was measured to 10.5 lbs. Then the applied compressive force was measured to 5.0 lbs at the same threshold value of the pressure sensitivity in the sympathetic tone-dependent point St. 18. At the same threshold value of the pressure sensitivity in the sympathetic tone-dependent point the applied compressive force was thus 48% of the applied compressive force in the sympathetic tone-neutral point. According to the present invention this corresponds to Level 2 stress.

Example 2c

The sympathetic tone of another person was determined in the following manner. By means of a manometer at a threshold value of the pressure sensitivity in the sympathetic tone-neutral point anteriorly on the upper side of the clavicle, the applied compressive force was measured to 14.0 lbs. Then the applied compressive force was measured to 5.0 lbs at the same threshold value of the pressure sensitivity in the sympathetic tone-dependent point, Per 1, and to 5.5 lbs in the sympathetic tone-dependent point St. 18. At the same threshold value of the pressure sensitivity in the sympathetic tone-dependent points the applied compressive force was thus 36% and 39%, respectively, of the applied compressive force in the sympathetic tone-neutral point. According to the present invention this corresponds to Level 2 stress.

Example 3

The sympathetic tone of a person was determined in the following manner: By means of a manometer at a threshold value of the pressure sensitivity in the sympathetic tone-neutral point anteriorly on the upper side of the clavicle, the applied compressive force was measured to 9.0 lbs. Then the applied compressive force was measured to 2.0 lbs at the same threshold value of the pressure sensitivity in the sympathetic tone-dependent point C.V. 17. At the same threshold value of the pressure sensitivity in the sympathetic tone-dependent point the applied compressive force was thus 22% of the applied compressive force in the sympathetic tone-neutral point. According to the present invention this corresponds to Level 3 stress.

Example 4

The person mentioned in example 3 was given a personally calibrated system according to the invention for measuring an applied compressive force for determining the sympathetic tone, said system including a measuring device and a scale, which in this example was divided into four zones corresponding to the four levels of stress, said system displaying the applied compressive force and provided with a marker for marking of one or more measuring points. By using the supplied system according to the invention, the person was able to determine his/her sympathetic tone at any convenient time. As a result the person was subsequently able to determine the sympathetic tone by observing to which zone an applied compressive force corresponded at the threshold value of the pressure sensitivity in a sympathetic tone-dependent point. One zone corresponds to less than 30% (Level 3); another zone corresponds to between 30% and less than 55% (Level 2); a third zone corresponds to between 55% and less than 80%; and a fourth zone corresponds to more than or equal to 80% of the applied compressive force at the threshold value of the pressure sensitivity in a sympathetic tone-neutral point.

Example 5

The sympathetic tone of a person was determined in the following manner: By means of a manometer at a threshold value of the pressure sensitivity in the sympathetic tone-neutral point anteriorly on the upper side of the clavicle, the applied compressive force was measured to 9.0 lbs. Then the applied compressive force was measured to 2.0 lbs at the same threshold value of the pressure sensitivity in the sympathetic tone-dependent point C.V. 17. At the same threshold value of the pressure sensitivity in the sympathetic tone-dependent point the applied compressive force was thus 22% of the applied compressive force in the sympathetic tone-neutral point. According to the present invention this corresponds to Level 3 stress. The person then filled-in a questionnaire about the person's stress level, said questionnaire showing that that the person displayed symptoms of chronic accumulated stress.

The threshold value of the pressure sensitivity was determined to "+++" by using a finger.

Four weeks later—after suitable intervention—the same measurings were repeated for the person.

By means of a manometer at a threshold value of the pressure sensitivity in the sympathetic tone-neutral point anteriorly on the upper side of the clavicle, the applied compressive force was measured to 10.0 lbs. Then the applied compressive force was measured to 9.5 lbs at the same threshold value of the pressure sensitivity in the sympathetic tone-dependent point C.V. 17. At the same threshold value of the pressure sensitivity in the sympathetic tone-dependent point the applied compressive force was thus 95% of the applied compressive force in the sympathetic tone-neutral point. According to the present invention this corresponds to Level 0 stress. The threshold value of the pressure sensitivity was determined to "0" by using a finger.

At the same time, the person advised that the previously recorded clinical signs of stress had passed.

Example 6

At a test with 250 randomly selected persons, the correlation between physiological stress and clinical stress was examined. The 250 randomly selected persons were told to fill out a questionnaire to ascertain whether they had experienced some specific situations within the last four weeks. There were 35 questions in total which represented different clinical signs of stress.

The persons were then instructed to examine themselves—in plenum—by initially identifying the upper side of the clavicle and there to register which intensity of an applied pressure was necessary to obtain the threshold value of the pressure sensitivity. With this as a starting point, the persons were instructed to locate C.V. 17 and based on the same procedure used on the upper side of the clavicle to determine the relative applied compressive force necessary to obtain the same threshold value of the pressure sensitivity on a four-point scale: 0, +, ++, +++.

All of the questionnaires were then collected and analysed.

The correlation between the applied compressive force to obtain the threshold value on the upper side of the clavicle in relation to C.V. 17 was significant ($p < 0.001$), ie. the more stress symptoms experienced by the individual person within the last four weeks the less compressive force was to be applied to the thorax in the point C.V. 17 in relation to the upper side of the clavicle.

Example 7

Prognostic Use of the Method/System

A completely healthy person, eg. a musician or conductor, employs the method and system each morning to ensure a low measurement, which prognostically gives an optimum utilization of his/her resources when music is to be played/conducted later in the day.

If one morning the measurement is high, the measurement allow for initiation of stress-reducing activities, such as exercise/relaxation. When the activity has been completed, the person can measure whether this has had a sufficient effect, ie. a low measurement is obtained. If the desired goal has not been met, the procedure may be repeated.

Example 8

Daily Stimulation with a Preventive Effect

As in example 7, the system in this example, however, also being used for performing the following actions:

By means of the system such a strong continuous pressure is maintained in a sympathetic tone-dependent point that the pressure is felt without the stimulation causing pain. After 20-40 seconds the person registers that the subjacent soreness has decreased.

By means of the system this can be recorded as a 50% increased pain threshold; The pain threshold may thus increase from 40% to 60% of the threshold value in the sympathetic tone-neutral point.

Physiologically, this entails that the "stress phase" has passed and the restitution phase is activated.

This action may contribute to preventing negative stress.

Example 9

Ad hoc Stimulation for Immediate Relief of Stress

As example 7, in this example, however, the user registers a high value and immediately performs the action as described in example 8. At a correctly performed action, the user will be able to register a likely 50% improvement in the measured value after 20-40 seconds.

Example 10

Measuring for Learning

As the method and system provide a here-and-now measurement of the stress level, ie. the activity in the sympathetic nervous system, a person is able known his/her "morning value" and repeat the measurings during the day so as to identify specific situations affecting the stress level (eg. a conversation, an order, a phone message, a task).

As the stress phase is activated within a few second and passes again within 20-40 seconds, the method and system provide completely new possibility for learning how different daily situations affect the stress level—both in negative and positive direction.

In the long view, the method is thus able to tell the person whether for instance a holiday has had the desired relaxing effect.

The invention claimed is:

1. A method of determining a sympathetic tone including the steps of:
   measuring an applied stimulation at a threshold value of the stimulation in one or more sympathetic tone-neutral points;
   measuring an applied stimulation at the same threshold value in one or more sympathetic tone-dependent points; and
   comparing a value of the measured applied stimulation in one of the one or more sympathetic tone-dependent points with a value of the measured applied stimulation in one of the one or more sympathetic tone-neutral points so as to determine the sympathetic tone.

2. The method according to claim 1, wherein the applied stimulation is provided by an applied mechanical stimulation.

3. The method according to claim 2, wherein the applied mechanical stimulation is provided by an applied compressive force.

4. The method according to claim 1, wherein the applied stimulation is provided by an applied thermal stimulation.

5. The method according to claim 4, wherein the applied thermal stimulation is provided by an applied heat or cold source.

6. The method according to claim 1, wherein the applied stimulation is provided by an applied radiation.

7. The method according to claim 6, wherein the applied radiation is provided by an applied infrared, visible and/or ultraviolet light or combined spectra thereof.

8. The method according to claim 1, wherein the applied stimulation is provided by an applied chemical stimulation.

9. The method according to claim 8, wherein the applied chemical stimulation is provided by an applied organic or inorganic compound.

10. The method according to any one of the preceding claims, wherein the determination is performed by a system for measuring the applied stimulation.

11. The method according to claim 1, wherein the measuring of an applied stimulation at a threshold value of the stimulation in one or more sympathetic tone-neutral points is carried out anteriorly on the upper side of the clavicle and/or posteriorly on the spinal column corresponding to TH 10-11.

12. The method according to claim 1, wherein the measuring of an applied stimulation at a threshold value of the stimulation is carried out in one or more sympathetic tone-dependent points at one or more locations on the skin which innervationally correspond to the nerve supply to the heart of the sympathetic nervous system.

13. The method according to claim 1, wherein the measuring of an applied stimulation at a threshold value of the stimulation in one or more sympathetic tone-dependent points is carried out in one or more of the points: C.V. 17 in the middle of the sternum and/or St 18 between two ribs below the nipple and/or Per 1 between the nipple and the anterior axillary fold and/or on the spinal column corresponding to TH 3-6, where the most sore point of the said points are chosen.

14. A method of use of a system for applying and measuring a stimulation for determining a sympathetic tone including the steps of:
  measuring an applied stimulation at a threshold value of the stimulation in one or more sympathetic tone-neutral points;
  measuring an applied stimulation at the same threshold value of the stimulation in one or more sympathetic tone-dependent points; and
  comparing a value of the measured applied stimulation in one of the one or more sympathetic tone-dependent points with a value of the measured applied stimulation in one of the one or more sympathetic tone-neutral points so as to determine the sympathetic tone.

15. The method according to claim 14, wherein the measuring of an applied stimulation at a threshold value of the stimulation in one or more sympathetic tone-neutral points is carried out on the upper side of the clavicle and/or on the spinal column corresponding to TH 10-11.

16. The method according to claim 14 or 15, wherein the measuring of an applied stimulation at a threshold value of the stimulation is carried out at one or more points on the skin, said points innervationally corresponding to the nerve supply to the heart from the sympathetic nervous system.

17. The method according to claim 14, wherein the measuring of an applied stimulation at a threshold value of the stimulation in one or more sympathetic tone-dependent points is carried out in one or more of the points: C.V. 17 in the middle of the sternum and/or St 18 between two ribs below the nipple and/or Per 1 between the nipple and the anterior requirement and/or on the spinal column corresponding to TH 3-6, where the most sore point of the said points is chosen.

18. The method according to claim 1, wherein the threshold value of stimulation is a threshold value at which the stimulation is perceived as pain.

19. The method according to claim 14, wherein the threshold value of stimulation is a threshold value at which the stimulation is perceived as pain.

* * * * *